United States Patent
Santomieri

[11] 3,938,530
[45] Feb. 17, 1976

[54] CATHETER
[76] Inventor: Louis S. Santomieri, 4517 San Marino Drive, Davis, Calif. 95616
[22] Filed: Nov. 15, 1974
[21] Appl. No.: 524,241

[52] U.S. Cl. .............................. 128/349 R; 128/243
[51] Int. Cl.² ................................. A61M 25/00
[58] Field of Search ........... 128/349 R, 350 R, 348, 128/243

[56] References Cited
UNITED STATES PATENTS
| | | | |
|---|---|---|---|
| 2,649,092 | 8/1953 | Wallace | 128/349 R |
| 3,108,595 | 10/1963 | Overment | 128/350 R |
| 3,799,172 | 3/1974 | Szpur | 128/349 R |

FOREIGN PATENTS OR APPLICATIONS
| | | | |
|---|---|---|---|
| 955,490 | 4/1964 | United Kingdom | 128/349 R |

*Primary Examiner*—Dalton L. Truluck
*Attorney, Agent, or Firm*—Roger B. Webster

[57] ABSTRACT

A retention-type catheter adapted to be inserted, through the urethra, into the urinary bladder of a medical patient; the catheter including—in unitary relation—a primary tube for drainage of the bladder, a secondary tube for irrigation of the bladder, and an initially contracted but expansible retainer formed in the primary tube adjacent the tip thereof, the secondary tube being longitudinally movable relative to the primary tube and arranged to further serve as an exteriorly manually actuated, pull-push element operative to cause expansion and contraction of such retainer, respectively.

4 Claims, 8 Drawing Figures

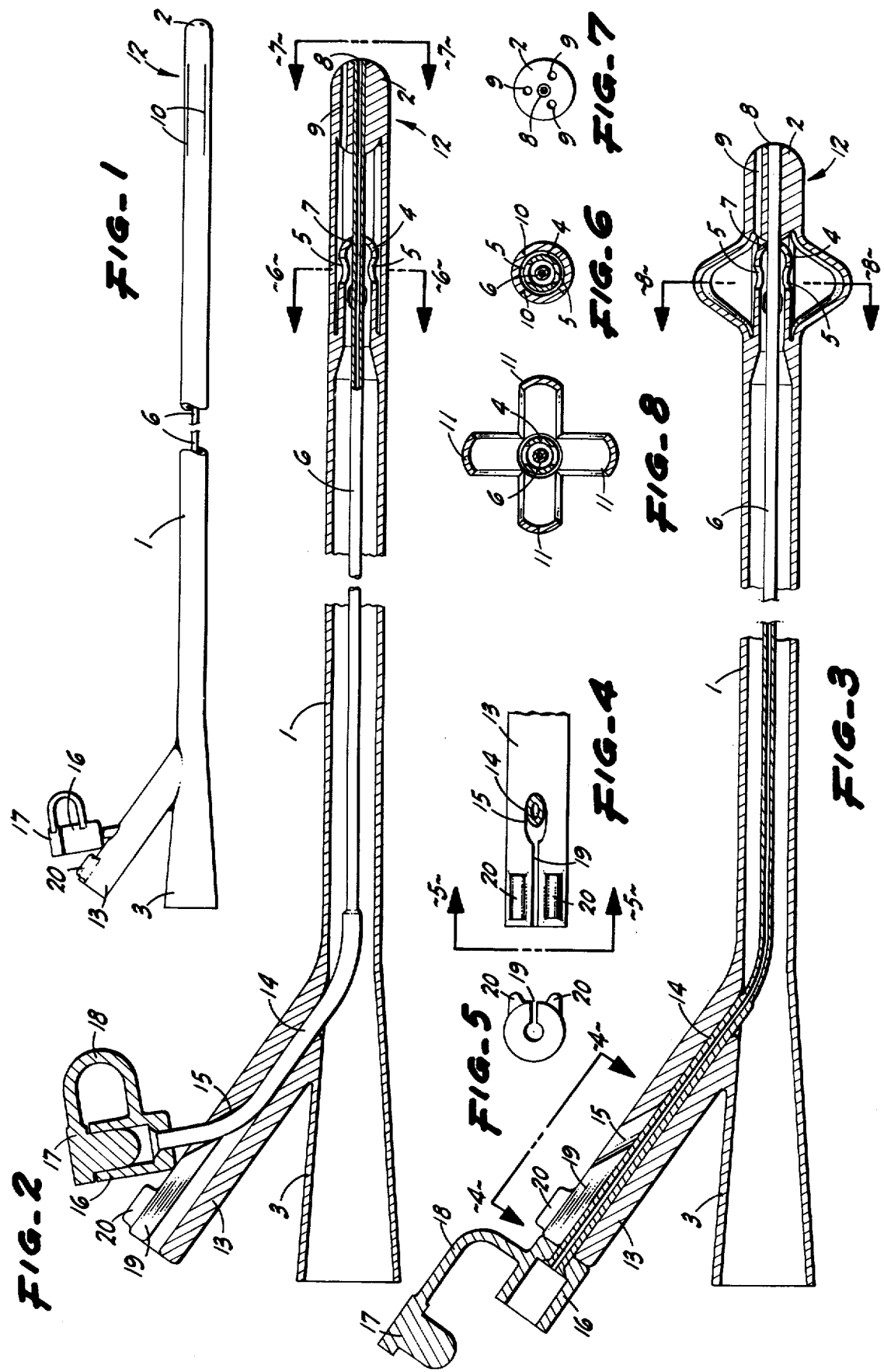

CATHETER

BACKGROUND OF THE INVENTION

Heretofore, retention catheters capable of bladder drainage and irrigation, and having expandable retention means, have frequently been unduly complex or cumbersome, unstable, difficult to manipulate, and not wholly satisfactory in their functional characteristics. The catheter of the present invention was conceived by me in a successful effort to overcome such problems.

SUMMARY OF THE INVENTION

The present invention provides, as an important object, a retention-type catheter, for insertion, through the urethra, into the urinary bladder of a medical patient; the catheter including, in unitary relation, a primary tube for drainage of the bladder, a secondary tube for irrigation of the bladder, and an initially contracted but expansible retainer formed in the primary tube adjacent the tip thereof, the secondary tube being longitudinally movable relative to the primary tube and arranged to further serve as an exteriorly manually actuated, pull-push element operative to cause expansion and contraction of such retainer.

The present invention provides, as another important object, a retention-type catheter, as above, which is simple and compact in its parts array, economical to manufacture, and extremely easy to manipulate and uses—this especially with the secondary tube—which is disposed mainly within the primary tube—having a dual purpose; i.e., firstly for bladder irrigation, and, secondly, to actuate the retainer.

The present invention provides, as a still further object, a practical, reliable, and durable catheter, and one which is exceedingly effective for the purpose for which it is designed.

BRIEF DESCRIPTION OF THE DRAWINGS

FIG. 1 is a side view of the catheter, with the retainer contracted; the view being foreshortened.

FIG. 2 is an enlarged sectional elevation of the same.

FIG. 3 is a view similar to FIG. 2, but shows the retainer expanded.

FIG. 4 is a fragmentary plan view on line 4—4 of FIG. 3.

FIG. 5 is an end view taken on line 5—5 of FIG. 4.

FIG. 6 is a cross section taken on line 6—6 of FIG. 2.

FIG. 7 is an end view on line 7—7 of FIG. 2.

FIG. 8 is a cross section on line 8—8 of FIG. 3.

DESCRIPTION OF THE PREFERRED EMBODIMENT

Referring now more particularly to the drawings and to the characters of reference marked thereon, the catheter, of the present invention, comprises—in the main of soft, flexible rubber—an elongated primary tube 1 having a closure tip 2 at its outer or forward end, and a relatively short but enlarged, tapered neck 3 at its rear end adapted for frictional plug-coupling to a drainage hose (not shown).

Within the confines thereof, and adjacent but initially spaced from the tip 2, the primary tube 1 is formed with a hollow internal tip 4 having a plurality of side holes 5 in circumferentially staggered relation; the internal tip 4, from the holes 5 forward, being of an outside diameter somewhat less than the inside diameter of the primary tube 1 whereby to provide clearance therebetween as shown.

A secondary tube 6 is disposed within the primary tube 1 and extends the length of the latter except at the rear portion as will later appear. The secondary tube 6, which is of substantially less outside diameter than the inside diameter of the primary tube 1 to provide necessary clearance, passes in guided slidable relation through an axial or central opening 7 in the internal tip 4, extends therefrom to, and in fixed relation through, the tip 2, and thence opens, as at 8, to the extremity of said tip 2.

A plurality of longitudinal "flashback" holes 9 are formed in the tip 2 from end to end thereof and in circumferentially spaced relation about the related portion of the secondary tube 6.

The primary tube 1—in the zone of the free or clearance portion of tip 4 and ahead thereof to the tip 2—is formed with a plurality of longitudinal, circumferentially arrayed slits 10 which define strips 11; the latter, of course, remaining end-connected to the primary tube. Such strips 11 initially lie in the normal plane of the primary tube 1, but, upon relative rearward movement of tip 2, such strips 11 fold or buckle outward and form an enlarged retainer, indicated generally at 12, of cruciate form in transverse elevation. As expanded (see FIGS. 3 and 8), the retainer 12 permits of liquid flow therethrough, into the internal tip 4 from holes 5, and thence into the primary tube 1 rearwardly of said internal tip.

The tip 2 is drawn rearwardly, to expand the retainer 12 as above described, by imparting rearward longitudinal movement to the secondary tube 6, and then releasably securing the same against return motion in order to maintain said retainer expanded as long as required. Such rearward movement and securing of the secondary tube 6 is accomplished through the medium of the following arrangement:

Immediately ahead of the rear, tapered neck 3 of the primary tube 1, the latter includes—in communication therewith—a short, rearwardly divergent guide tube 13; the rear portion 14 of the secondary tube 6 curving and thence extending in slidable relation into said guide tube 13. Such rear portion 14 of the secondary tube 6 is, as shown, somewhat enlarged in diameter to prevent kinking under thrust, and engages in the guide tube 13 in relatively close, anti-leak, sealing relation although remaining slidable therein.

The enlarged rear portion 14 initially extends only part way along the guide tube 13, and intermediate the ends of the latter bends into and runs out through an outwardly diagonal opening 15 in the outer wall of such guide tube. Exteriorly of the guide tube 13, the exposed rear end of the enlarged rear portion 14 of the secondary tube 6 is fitted, and bottom-communicates, with a socket head 16 initially closed by a removable plug 17 connected to the head 16 by a small, integral, flexible strap 18; the socket head initially resting on the side of said guide tube 13. In this position of the parts, the secondary tube 6 is disposed with the tip 2 non-retracted.

From the opening 15 to the rear or free end of the guide tube 13, such tube is formed on the outer side with a longitudinal, open-ended slot 19; there being upstanding finger tabs 20 on the guide tube 13 at opposite sides of the slot 19.

In use of the described catheter, the latter is inserted through the urethra with the retainer then contracted as shown in FIGS. 1 and 2. Upon the tip 2 entering the bladder of the patient, urine will first escape through the "flashback" holes 9, and then flow in the primary tube 1, and from the latter into the drainage tube (not shown) coupled to the tapered neck 3 of said primary tube. This initial flow alerts the physician to the fact that entry into the bladder has been accomplished, and—thereupon—the retainer 12 is expanded in the bladder for the purpose of catheter retention. The manipulative steps employed to expand the retainer are as follows:

Firstly, the finger tabs 20 are engaged and spread apart (the guide tube 13 being flexible and resilient) to increase the width of the slot 19; the socket head 16 then being grasped and pulled rearwardly, causing the adjacent part of the enlarged portion 14 of the secondary tube to be drawn rearward in, and to finally escape from the rear end of such slot. Nextly, the socket head 16 is abutted, in stop-relation, against the rear or outer end of the guide tube 13. When the socket head 16 is thus pulled rearwardly, a corresponding rearward movement—guided by internal tip 4—is imparted to the secondary tube 6, and the tip 2 is shifted rearwardly a distance sufficient to expand the retainer; the socket head 16, as then in its stop position against the guide tube 13, holding the secondary tube 6 and the tip 2 in retainer-expanding position. With the retainer 12 expanded, the catheter serves its normal drainage function, with urine passing through both the holes 9 and said expanded retainer.

Obviously, to release the retainer, it is caused to contract by merely reversing the steps, as above described, employed for expansion of the retainer.

As will be apparent, the secondary tube 6 serves, in effect, as a pull-push element in the manipulation attendant expansion and contraction, respectively, of the retainer 12.

With the catheter in place and the retainer expanded, irrigation of the bladder can be readily accomplished in the following manner:

The plug 17 is first removed from the socket head 16, and a supply tube (not shown) carrying a flow-regulated liquid (for bladder irrigation) is plug-connected to said socket head 16 and hence in communication with the secondary tube 6. After passage through the secondary tube, the liquid delivers from the discharge end 8 thereof and into the patient's bladder.

With the catheter constructed as described, it will be recognized that in addition to the advantage of drainage by one tube and irrigation by another tube, these functions can be simply and effectively performed, with the further advantage that the retainer can be expanded and contracted by means of said other tube—thus not only simplifying the unitary parts array and cost of the catheter, but also providing for greater ease of manipulation thereof.

From the foregoing description, it will be readily seen that there has been produced such a catheter as substantially fulfills the objects of the invention, as set forth herein.

While this specification sets forth in detail the present and preferred construction of the catheter, still in practice such deviations from such detail may be resorted to as do not form a departure from the spirit of the invention as defined by the appended claims.

I claim:

1. In a soft, flexible, retention-type catheter which includes a primary tube having an outer-end tip, and an initially contracted but expandable retainer formed in the tube adjacent the tip and adapted to be expanded and contracted by rearward and forward movement, respectively, of said tip; a relatively smaller diameter secondary tube disposed within the primary tube in longitudinally movable relation, the forward end of the secondary tube being secured to the tip and open thereat, and means connected to the rear end of the secondary tube exteriorly of the primary tube adapted for manipulation to impart such rearward and forward movement to the tip through the medium of said secondary tube serving as a pull-push element; the primary tube including, in communication and adjacent its rear end, a short, lateral, rearwardly divergent guide tube, the secondary tube extending into the guide tube in slidable relation, and said means being a head on the secondary tube at its rear end; said secondary tube initially leading out of the guide tube through a side opening therein intermediate its ends and with the head disposed exteriorly of and to the side of said guide tube, the tip then being in forwardly moved position with the retainer contracted, the guide tube having an open-ended, longitudinal slot therein extending from its rear end to such side opening, the slot being of a width to normally prevent the related portion of the secondary tube to move through such slot, the guide tube being flexible and resilient whereby to permit its manipulation to widen the slot sufficient for said related portion of the secondary tube to pass rearwardly through the slot to a position extending longitudinally within the guide tube and with the head abutting the rear end of said guide tube, the tip then being in a rearwardly moved position with the retainer expanded.

2. In a soft, flexible, retention-type catheter which includes a primary tube having an outer-end tip, an initially contracted but expandable retainer formed in the primary tube adjacent the tip and adapted to be expanded and contracted by rearward and forward movement, respectively, of said tip, a relatively small diameter secondary tube disposed within the primary tube in longitudinally movable relation, the forward end of the secondary tube being secured to the tip and open thereat, and the rear end of the secondary tube exteriorly of the primary tube being adapted for manipulation to impart such rearward and forward movement to the tip through the medium of said secondary tube serving as a pull-push element; the improvement characterized by an internal tip formed in the primary tube adjacent but short of the outer-end tip, the internal tip having a central opening therein through which the secondary tube extends in slidable, guided relation.

3. A catheter, as in claim 2, in which the internal tip is disposed in substantially the zone of the retainer, the latter when expanded permitting of liquid flow therethrough into the primary tube and to said intermediate tip, and such internal tip being hollow and having liquid-flow holes therein.

4. A catheter, as in claim 3, in which the outer-end tip is formed with longitudinal "flashback" openings therethrough; the internal tip, from the openings therein and forwardly thereof, being free of and having liquid-flow clearance with the primary tube.

\* \* \* \* \*